(12) United States Patent
Manwaring et al.

(10) Patent No.: US 9,962,294 B2
(45) Date of Patent: May 8, 2018

(54) PATTERNED NEO-EPITHELIALIZATION DRESSINGS, SYSTEMS, AND METHODS

(71) Applicant: KCI LICENSING, INC., San Antonio, TX (US)

(72) Inventors: Michael Manwaring, San Antonio, TX (US); Braden K. Leung, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 27 days.

(21) Appl. No.: 15/170,585

(22) Filed: Jun. 1, 2016

(65) Prior Publication Data

US 2016/0270960 A1    Sep. 22, 2016

Related U.S. Application Data

(63) Continuation of application No. 13/045,302, filed on Mar. 10, 2011, now Pat. No. 9,358,158.

(60) Provisional application No. 61/314,274, filed on Mar. 16, 2010, provisional application No. 61/314,236, filed on Mar. 16, 2010.

(51) Int. Cl.
  *A61F 13/00* (2006.01)
  *A61M 1/00* (2006.01)

(52) U.S. Cl.
  CPC .. *A61F 13/00021* (2013.01); *A61F 13/00063* (2013.01); *A61M 1/0088* (2013.01); *A61F 13/00068* (2013.01); *A61F 2013/00089* (2013.01); *A61M 2210/04* (2013.01)

(58) Field of Classification Search
  CPC .... A61F 2013/0054; A61F 2013/00217; A61F 2013/00536; A61F 13/00; A61F 13/02; A61M 35/006; A61M 1/0088; A61M 1/0023; A61M 35/00; A61M 35/003; A61K 8/0208; A61B 19/42
  See application file for complete search history.

(56) References Cited

U.S. PATENT DOCUMENTS 1,355,846 A    10/1920   Rannells
2,547,758 A    4/1951    Keeling
(Continued)

FOREIGN PATENT DOCUMENTS

AU    550575 B2    3/1986
AU    745271 B2    3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
(Continued)

*Primary Examiner* — Ophelia A Hawthorne

(57) ABSTRACT

Systems, methods, and apparatuses are presented that involve forming patterns on neo-epithelium that allow increased functionality and may more nearly resemble the original epithelium. In one instance, a patterned neo-epithelium dressing for treating a tissue site having granulation tissue includes an interface member for placing proximate the granulation tissue and a plurality of three-dimensional features formed on a second, patient-facing side of the interface member. Other systems, methods, and apparatuses are disclosed.

19 Claims, 5 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0032762 A1* | 2/2007 | Vogel .................. A61F 13/0216 604/305 |
| 2007/0225663 A1* | 9/2007 | Watt .................... A61M 1/0088 604/313 |
| 2008/0275409 A1* | 11/2008 | Kane .................... A61F 13/0203 604/305 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

(56) References Cited

OTHER PUBLICATIONS

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

PATTERNED NEO-EPITHELIALIZATION DRESSINGS, SYSTEMS, AND METHODS

RELATED APPLICATION

This application is a continuation of U.S. patent application Ser. No. 13/045,302, filed Mar. 10, 2011, which issued as U.S. Pat. No. 9,358,158, which claims the benefit, under 35 USC § 119(e), of the filing of U.S. Provisional Patent Application Ser. No. 61/314,274, entitled "Patterned Neo-Epithelialization Dressings, Systems, and Methods," filed 16 Mar. 2010, and U.S. Provisional Patent Application Ser. No. 61/314,236, entitled "Epithelialization Methods, Dressings, and Systems," filed 16 Mar. 2010. The entire disclosures of the above applications are incorporated herein by reference.

BACKGROUND

The present disclosure relates generally to medical treatment systems and, more particularly, to patterned neo-epithelialization dressings, system, and methods.

Depending on the medical circumstances, reduced pressure may be used for, among other things, reduced-pressure therapy to encourage development of granulation tissue at a tissue site. Granulation tissue is connective tissue that forms on wounds during tissue repair. Granulation tissue is typically defined to include new blood vessels, immune cells, fibroblasts, and provisional extracellular matrix. Granulation tissue typically signals the proliferative phase of wound healing. Reduced-pressure therapy typically involves manifolding, or distributing, reduced pressure to the tissue site.

SUMMARY

An illustrative, non-limiting embodiment of a system for treating a wound having granulation tissue on a patient includes a patterned neo-epithelium dressing for disposing proximate the wound. The patterned neo-epithelium dressing for treating a wound having granulation tissue includes an interface member having a first side and a second, patient-facing side for placing proximate to the granulation tissue and a plurality of three-dimensional features formed on the second, patient-facing side of the interface member. The system further includes a sealing member for placing over the patterned neo-epithelium dressing and the patient's epidermis, a reduced-pressure interface fluidly coupled to the sealing member, and a reduced-pressure source fluidly coupled to the reduced-pressure interface.

An illustrative, non-limiting embodiment of a patterned neo-epithelium dressing for treating a wound having granulation tissue includes an interface member having a first side and a second, patient-facing side for placing proximate the granulation tissue and a plurality of three-dimensional features formed on the second, patient-facing side of the interface member.

An illustrative, non-limiting embodiment of a method of treating a wound site of a patient includes optionally forming granulation tissue at the wound site, deploying a patterned neo-epithelium dressing proximate the granulation tissue, and applying a contact pressure on the patterned neo-epithelium dressing. The patterned neo-epithelium dressing for treating a wound having granulation tissue includes an interface member having a first side and a second, patient-facing side for placing proximate the granulation tissue. The patterned neo-epithelium dressing also includes a plurality of three-dimensional features formed on the second, patient-facing side of the interface member.

An illustrative, non-limiting embodiment of a method of treating a wound site of a patient includes directing flow of endogenous fluids to cause patterned protein deposition, causing guidance of the migrating epithelium on the patterned deposition of proteins to form a neo-epithelium, and forming fissures in the neo-epithelium.

An illustrative, non-limiting embodiment of a method of manufacturing a patterned neo-epithelium dressing for treating a wound having granulation tissue includes forming an interface member having a first side and a second, patient-facing side for placing proximate the granulation tissue, and forming a plurality of three-dimensional features on the second, patient-facing side of the interface member.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
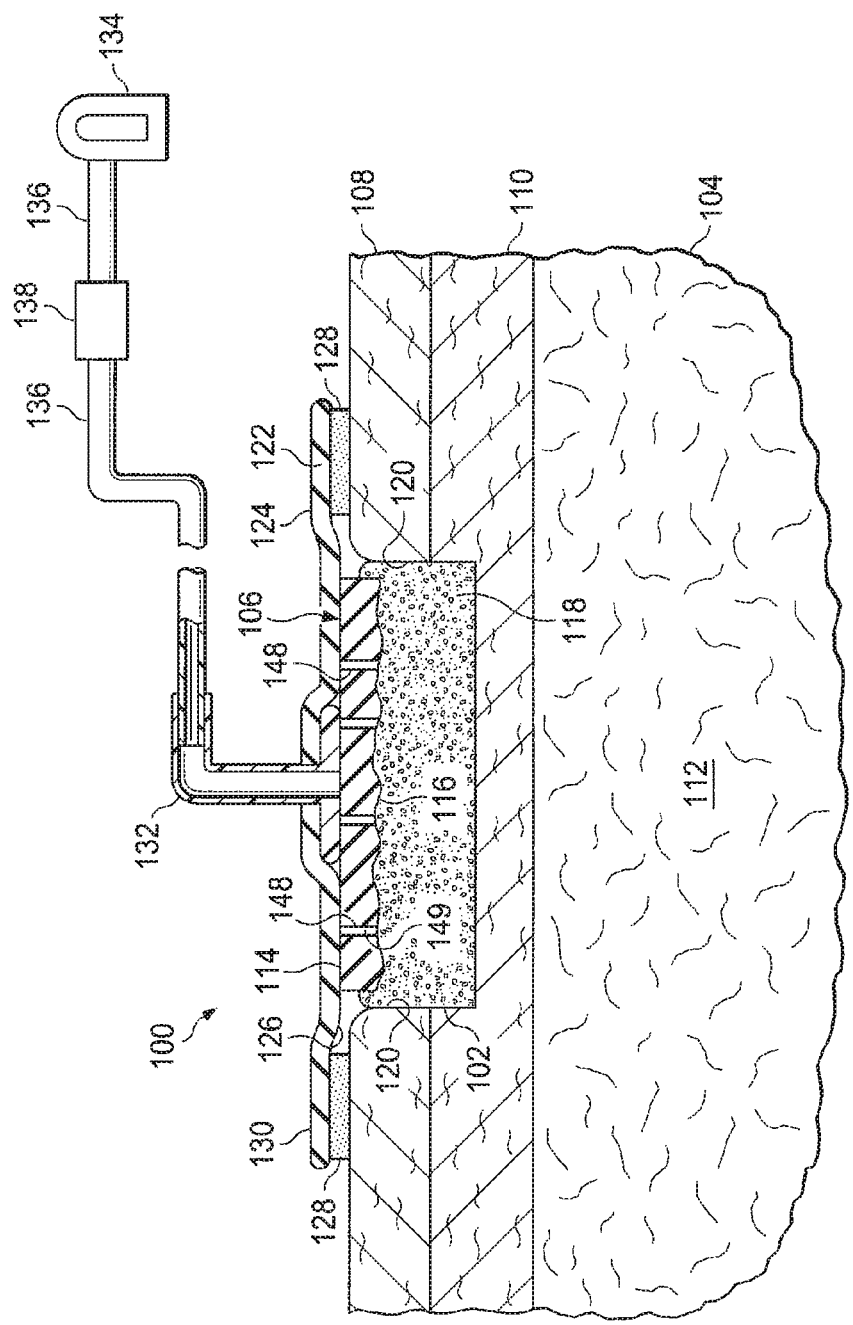
FIG. 1 is a schematic diagram with a portion shown in cross section of an illustrative, non-limiting embodiment of a system for treating a wound on a patient.

Referring primarily to FIGS. 1-4, and initially to FIG. 1, a system 100 for treating a wound 102 on a patient 104 that includes a patterned neo-epithelium dressing 106 is presented. The wound 102 may extend through epidermis 108 and into dermis 110. In some instances, the wound 102 extends into subcutaneous tissue 112. In the illustrative embodiment, the patterned neo-epithelium dressing 106, which has a first side 114 and a second, patient-facing side 116, is shown with the second, patient-facing side 116 against granulation tissue 118. As will be described further below, neo-epithelium tissue will grow from wound edges 120 and is directed and formed under the influence of the patterned neo-epithelium dressing 106.

A sealing member 122 forms a fluid seal over the patterned neo-epithelium dressing 106. "Fluid seal," or "seal," means a seal adequate to maintain reduced pressure at a desired site given the particular reduced-pressure source or subsystem involved. The sealing member 122 has a first side 124 and a second, patient-facing side 126. The sealing member 122 may be any material that provides a fluid seal. The sealing member 122 may, for example, be an impermeable or semi-permeable, elastomeric material. "Elastomeric" means having the properties of an elastomer and generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Additional, specific examples of sealing member materials include a silicone drape, 3M Tegaderm® drape, acrylic drape such as one available from Avery Dennison.

An attachment device 128 may be used to hold the sealing member 122 against the patient's epidermis 108 or another layer, such as a gasket or additional sealing member. The attachment device 128 may take numerous forms. For example, the attachment device 128 may be a medically acceptable, pressure-sensitive adhesive that extends about a periphery 130, a portion of, or the entirety of the sealing member 122.

A reduced-pressure interface 132 is fluidly coupled to the second, patient-facing side 126 of the sealing member 122. Reduced pressure developed by a reduced-pressure source 134 is delivered through a reduced-pressure delivery conduit 136 to the reduced-pressure interface 132. In one illustrative embodiment, the reduced-pressure interface 132 is a T.R.A.C.® Pad or Sensa T.R.A.C.® Pad available from KCI of San Antonio, Tex. The reduced-pressure interface 132 allows the reduced pressure to be delivered to the second, patient-facing side 126 of the sealing member 122 and ultimately to the patterned neo-epithelium dressing 106.

The reduced-pressure source 134 provides reduced pressure. The reduced-pressure source 134 may be any device for supplying a reduced pressure, such as a vacuum pump, wall suction, micro-pump, or other source. While the amount and nature of reduced pressure applied to a tissue site will typically vary according to the application, the reduced pressure will typically be between −5 mm Hg and −500 mm Hg and more typically between −50 mm Hg and −200 mm Hg. For example, and not by way of limitation, the pressure may be −90, −100, −110, −120, −130, −140, −150, −160, −170, −180, −190, −200 mm Hg or another pressure.

In some embodiments, before the patterned neo-epithelium dressing 106 is deployed on granulation tissue 118. The granulation tissue 118 may be developed using the system 100 but with a manifold (not shown) in the location where the patterned neo-epithelium dressing 106 is presently shown. The term "manifold" as used herein generally refers to a substance or structure that is provided to assist in applying reduced pressure to, delivering fluids to, or removing fluids from the wound 102. The manifold typically includes a plurality of flow channels or pathways that distribute fluids provided to and removed from the tissue site around the manifold. In one illustrative embodiment, the flow channels or pathways are interconnected to improve distribution of fluids provided to or removed from the wound 102. The manifold may be a biocompatible material that is capable of being placed in contact with the wound 102 and distributing reduced pressure to the wound 102. Examples of manifolds may include, for example, without limitation, devices that have structural elements arranged to form flow channels, such as, for example, cellular foam, open-cell foam, porous tissue collections, liquids, gels, and foams that include, or cure to include, flow channels. The manifold may be porous and may be made from foam, gauze, felted mat, or any other material suited to a particular biological application. In one embodiment, the manifold is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the wound 102, the actual pressure applied to the wound 102 may be more than the pressure normally associated with a complete vacuum. Consistent with the use herein, an increase in reduced pressure or vacuum pressure typically refers to a relative reduction in absolute pressure.

The reduced-pressure conduit 136 may have one or more devices, such as device 138. For example, the device 138 may be a fluid reservoir, or collection member, to hold exudates and other fluids removed. Other examples of devices 138 that may be included on the reduced-pressure conduit 136 or otherwise fluidly coupled to the reduced-pressure conduit 136 include the following non-limiting examples: a pressure-feedback device, a volume detection system, a blood detection system, an infection detection system, a flow monitoring system, or a temperature monitoring system.

Figure 2:
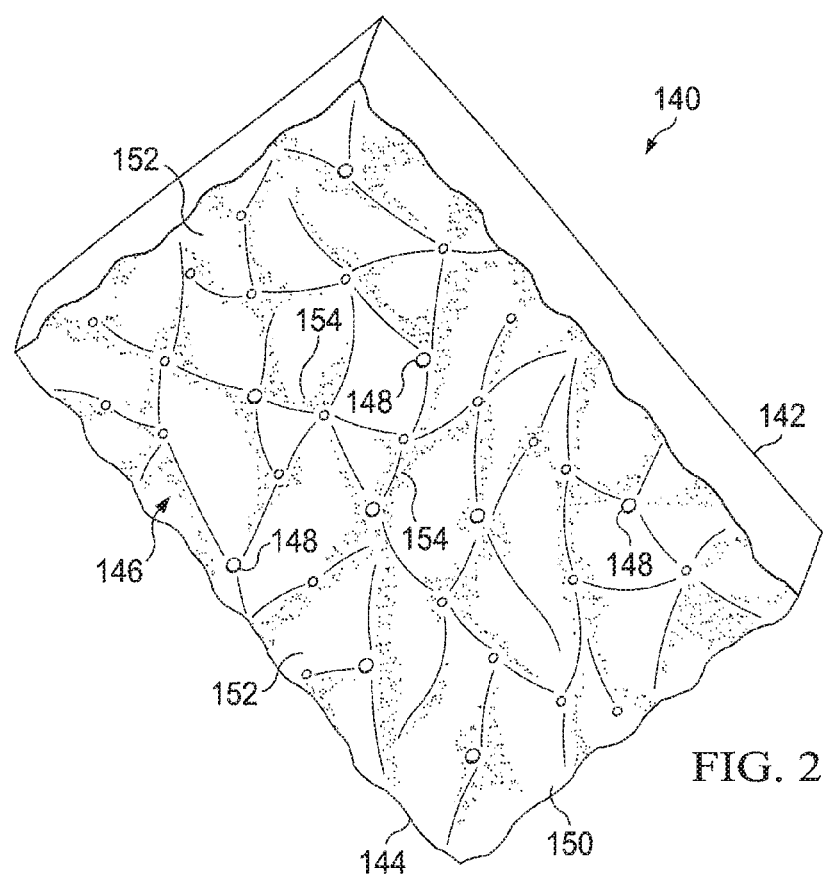
FIG. 2 is a schematic, perspective view of an illustrative, non-limiting embodiment of a patterned neo-epithelium dressing.
Figure 3:
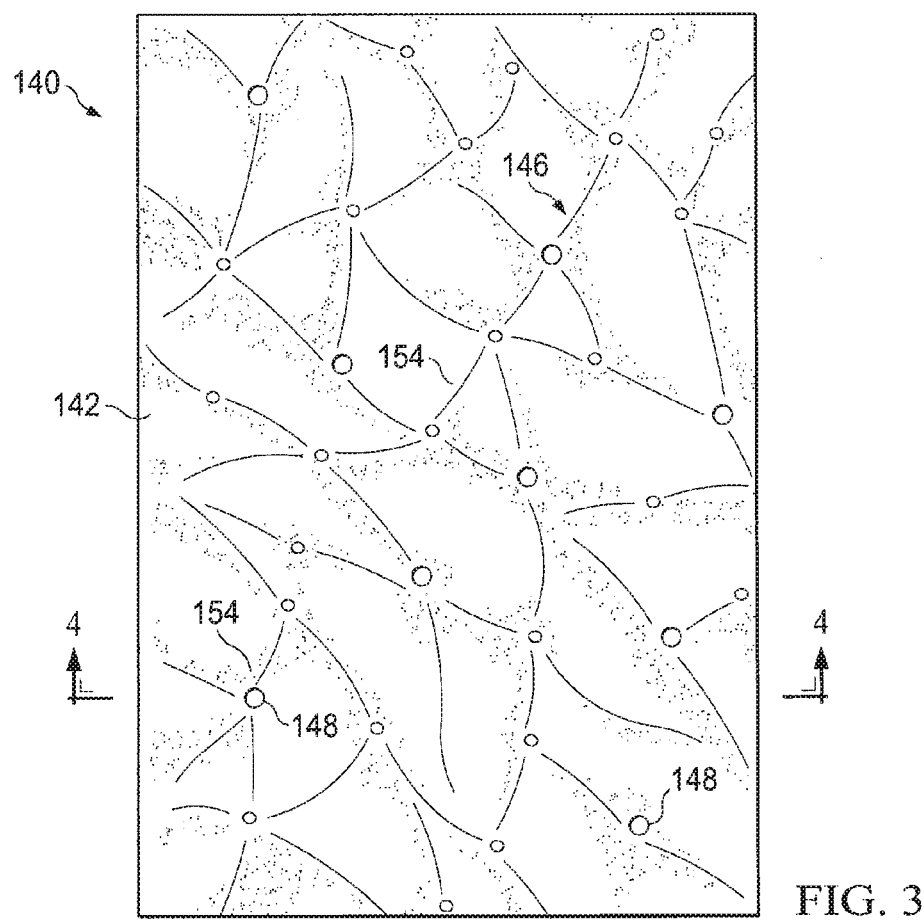
FIG. 3 is a schematic, bottom view of the patterned neo-epithelium dressing of FIG. 2.
Figure 4:
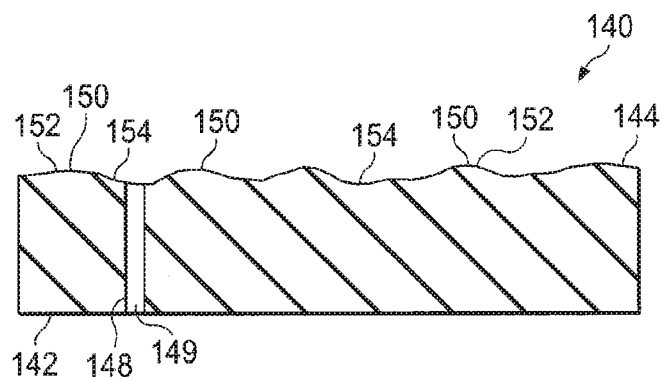
FIG. 4 is a schematic, cross-sectional view of the patterned neo-epithelium dressing of FIG. 3 taken along line 4-4.

Referring now primarily to FIGS. 2-4, the patterned neo-epithelium dressing 106 has an interface member 140 having a first side 142 and a second, patient-facing side 144 for placing proximate the granulation tissue 118 and a plurality of three-dimensional features 146 formed on the second, patient-facing side 144 of the interface member 140. The interface member 140 may be formed from any medical-grade polymers, thermoplastic polymers, resorbable polymers or materials, biologically derived polymers such as collagen, or other suitable materials, e.g., silicones, polyurethane films. The interface member 140 may also be formed using foam, for example, the embodiment shown in FIGS. 6A and 6B. The interface member 140 may be formed by casting, molding, or other techniques that form the interface member 140. As used herein, unless otherwise indicated, "or" does not require mutual exclusivity.

The interface member 140 has a plurality of pores large enough to allow fluid transmission and small enough to limit cell migration through the pores. The average pore size is below the minimum size through which cells are typically capable of migrating (giving the interface member 140 a relatively "smooth" overall texture in many embodiments) to prevent tissue ingrowth into the interface member 140 and to promote lateral cell migration parallel to a surface 150 of the interface member 140. Select pores may exceed the minimum size for cell migration, but be contained in sufficiently low density on the material surface to maintain acceptable levels of non-adherence to the wound 102. The average pore size remains in the acceptable range. At the other end of the range of the pore size, to allow for fluid control of the wound 102, pores of adequate size to allow for fluid transmission are typically incorporated throughout the interface member 140 or in organized patterns on the interface member 140 for promoting direct fluid flow. In one embodiment, the interface member may have a plurality of pores having an average pore size greater than 5 micrometers or microns (μm) and smaller than 1000 μm. In other non-limiting embodiments, the average pore size may be 10, 40, 80, 100, 120, 150, 200, 250, 300, 350, 400, 450, 500, 550, 600, 650, 700, 750, 800, 850, 900, or 950 μm or any dimension between these or other sizes. While the term "pore" is used, it should be understood that the pores may include slits or other apertures. Where dimensions of pores are specifically given, a generally round pore should be understood and the dimension applies to the diameter.

The formation process of the interface member 140 may form the plurality of three-dimensional features 146 or the three-dimensional features 146 may be formed separately and then coupled as part of the interface member 140. In another embodiment, the plurality of three-dimensional features 146 may be chemically etched, imprinted, or formed later as an aspect of the interface member 140.

The interface member 140 is formed with one or more fluid passageways 148, such as channels 149, that fluidly couple the first side 142 and second, patient-facing side 144 of the interface member 140. The fluid passageways 148 may be apertures, conduits, or inherent porous pathways in the subsisting material of the interface member 140.

The three-dimensional features 146 may include a plurality of ridges 152 or a plurality of grooves 154. The three-dimensional features 146 help direct the flow of fluids, e.g., endogenous fluids, such as exudates, to one or more of the fluid passageways 148. The three-dimensional features 146 or a portion of the three-dimensional features 146 may be coated with one or more proteins, e.g., growth factors, integrins, integrin receptors, antibodies, peptides, aptomers, or other suitable materials.

The three-dimensional features 146 may be formed as a pattern on the surface 150 that mimics or substantially replicates a human skin pattern. At least three approaches may be used to develop the pattern for the three-dimensional features 146. First, a "generic human skin pattern" may be used that includes a pattern that is modeled on a general or generic pattern for human skin. This pattern may not be specific to a particular location on a body, but is a more general pattern having wrinkles and general features.

Second, a "location-specific human skin pattern" may be used. With this second approach, a general skin pattern is used that is patterned on the general features for a specific area of a body. For example, a generic representation of skin on the back of a hand may be used for wound on the back of a hand.

Third, an "intact analogous human skin pattern" may be used. With this third approach, the pattern may be developed based on the specific patient's skin near the wound or on a duplicate body part. The pattern mimics or substantially replicates the skin near the wound or on the duplicate body part. For example, if a wound were on the back of the patient's left hand, either skin near the wound would be used as a model or the intact skin on the right hand would be used to form the three-dimensional features 146. This latter approach produces a custom symmetric dressing. In still other embodiments, the three-dimensional features 146 may be organized in other patterns such as a radial pattern to direct migration from a periphery to a center of the patterned neo-epithelium dressing 106.

Figure 5:
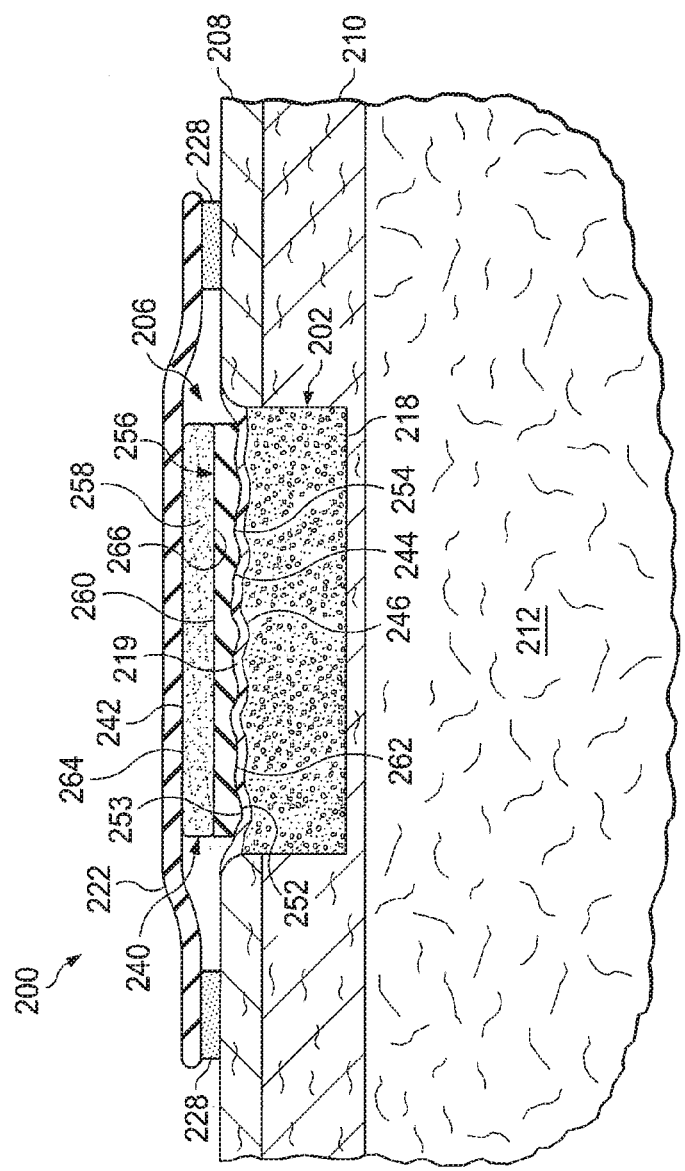
FIG. 5 is a schematic, cross-sectional view of an illustrative, non-limiting embodiment of a patterned neo-epithelium dressing.

Referring now primarily to FIG. 5, another illustrative embodiment of a system 200 for treating a wound 202. The system 200 is analogous in many respects to system 100 of FIG. 1 and analogous elements have been indicated by indexing the reference numerals by 100. The wound 202 is shown going through epidermis 208 and dermis 210 and almost into subcutaneous tissue 212. Granulation tissue 218 is formed on the bed of the wound 202 and neo-epithelium 219 is shown formed over the granulation tissue 218.

The system 200 includes a patterned neo-epithelium dressing 206 that includes an interface member 240, which has a first side 242 and a second, patient-facing side 244. The interface member 240 includes a thin member 256 and a foam member 258. The thin member 256, such as a polyurethane film or member made from other materials listed herein, has a first side 260 and a second, patient-facing side 262. The foam member 258 has a first side 264 and a second, patient-facing side 266. The first side 260 of the thin member 256 is adjacent to the second, patient-facing side 266 of the foam member 258 and may be coupled thereto by any known technique, including without limitation welding (e.g., ultrasonic or RF welding), flame lamination, bonding, adhesives, or cements. The thin member 256 may be formed from any medical-grade polymers, thermoplastic polymers, resorbable polymers or materials, biologically derived polymers such as collagen, or other suitable materials, e.g., silicones, polyurethane films.

A plurality of three-dimensional features 246 may be formed on the second, patient-facing side 262 of the thin member 256. The three-dimensional features 246 may be formed by imprinting, etching, or casting, or other techniques onto the thin member 256. As before, the three-dimensional features 246 may include a plurality of ridges 252 or a plurality of grooves 254. The three-dimensional features 246 may be formed as a pattern on the surface that mimics or substantially replicates a human skin pattern.

A contact pressure, or an inward pressure, is developed on the patterned neo-epithelium dressing 206. In this embodiment, the contact pressure is developed using the foam member 258 as a bolster and applying a sealing member 222 over the foam member 258 to create the contact force. Reduced pressure could also be used in the system 100 of FIG. 1. An attachment device 228 may be used to form a fluid seal with the sealing member 222 and the patient's epidermis 208.

The second, patient-facing side 244 and the first side 242 of the interface member 240 are in fluid communication through pores, which form fluid passageways, in the interface member 240. In addition to the pores or alternatively, channels (not shown but analogous to channels 149 in FIG. 1) may be formed.

The foam member 258 may be a hydrophilic foam that wicks fluids from the thin member 256. The foam member 258 may be an open-cell foam. In still another embodiment, the foam member 258 may be hydrophobic foam.

Figure 6A:
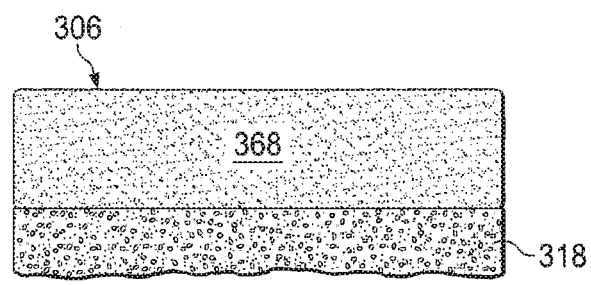
FIG. 6A is a schematic, cross-sectional view of an illustrative, non-limiting embodiment of a patterned neo-epithelium dressing shown without reduced pressure applied.
Figure 6B:
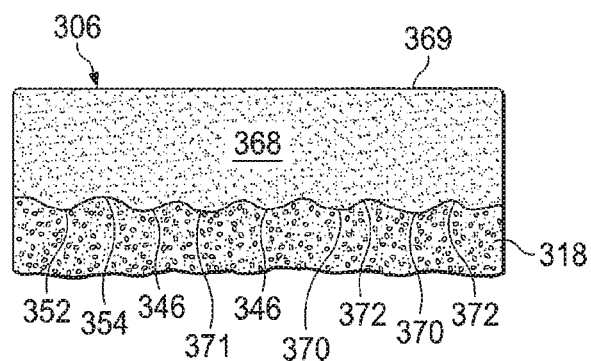
FIG. 6B is the patterned neo-epithelium dressing of FIG. 6A shown with reduced pressure applied.

Referring now primarily to FIGS. 6A and 6B, another illustrative, non-limiting embodiment of a patterned neo-epithelium dressing 306 is presented on granulation tissue 318. The patterned neo-epithelium dressing 306 is formed from a foam 368 having rigid portions 370 and less rigid portions 372 that are apparent under reduced pressure as shown in FIG. 6B. Because of the differing rigidity, the foam 368 forms a plurality of three-dimensional features 346 in the form of ridges 352 and grooves 354 when placed under reduced pressure. A first side 369 and a second, patient-facing side 371 are in fluid communication via fluid passageways formed by open cells in the foam 368. The three-dimensional features 346 may be formed as a pattern on the surface that mimics or substantially replicates a human skin pattern.

Referring now to FIGS. 1-6B, in use, according to one illustrative embodiment, granulation tissue 118, 218, 318 may be formed by placing the manifold (not shown) proximate the wound 102, 202 and forming a fluid seal using a sealing member 122, 222. Reduced pressure is applied to facilitate formation of the granulation tissue 118, 218, 318. Alternatively, the granulation tissue may be formed without assistance. As the granulation tissue 118, 218, 318 is formed, the patterned neo-epithelium dressing 106, 206, 306 may be placed proximate the granulation tissue 118, 218, 318 and covered by the sealing member 122, 222 to transition from granulation to epithelialization. Contact pressure is developed by using reduced pressure, a pressure wrap, a foam bolster with tensioning member or sealing member pressing on the bolster.

In many embodiments, reduced pressure is used to hold contact pressure and to remove fluids through the fluid passageways 148. The reduced pressure pulls endogenous fluids from the wound 102, 202 directed by the three-dimensional features 146 to the fluid passageways 148. As the endogenous fluids flow along the path directed by the three-dimensional features 146, patterned proteins or extra-cellular matrix (ECM), (e.g., fibrin or collagen) are deposited or formed. As migrating epithelium migrates from the wound edges 120, the epithelium is guided by the patterned protein deposition and forms the neo-epithelium in the desired pattern. The ridges 152 form fissures (e.g., fissures 253 in FIG. 5) in the neo-epithelium. These fissures or grooves in the neo-epithelium act as points of stress relief for flexion when exposed to bodily movement. The formation of the neo-epithelium in this way involves tissue formation according to the integrated principles of fluid flow, contact guidance, microstrain, and mechanotransduction.

In one embodiment, contact pressure is provided without reduced pressure. In this instance, the three-dimensional features 146 may be used primarily to direct cell migration. In addition, a hydrophilic member may be used to help manage fluids.

The patterned neo-epithelium dressing 106, 206 may influence protein adhesion, cell behavior (migration), and ECM production by the surface topography, or the three-dimensional features 146. The three-dimensional features 146 may also influence orientation of cells and ECM within the granulation tissue and thereby the neo-epithelium. In this manner, the features transmit contact guidance to a pericellular (cell-derived) matrix. The fibroblasts of the granulation tissue 118, 218 may start to align when placed in contact with the grooves 154 or ridges 152 of the patterned neo-epithelium dressing 106. The fibroblasts may align cytoskeleton, or the scaffolding, in substantially the same direction as directed by the three-dimensional features 146 of the patterned neo-epithelium dressing 106. The keratinocytes may follow the pattern expressed by the fibroblasts.

The fissures formed mimic those in intact skin. The three-dimensional features 146, 246 direct elements within the granulation tissue 118, 218 of healing wounds that could translate to the development of the overlying neo-epithelium 219 and result in a patterned epithelium with appropriate creases or fissures and ECM deposition for improved regeneration and functionality, including physiologically-equivalent flexion of the tissue and aesthetic appearance. This flexion is supported by the patterned deposition of ECM both within the underlying granulation layers and in the neo-epithelium. These structures provide points of stress relief and structural support to enhance bodily movement. In addition, the rate of re-epithelialization may be increased using the systems 100, 200. Another possible explanation for the re-epithelialization with the patterned neo-epithelium dressings 106, 206, 306 is that the directed fluid flow by the three-dimensional features 146, 246, 346 may lead to deposition of structural proteins in a haptotactic or chemotactic gradient, which could enhance the rate of outgrowth of keratinocytes.

In other embodiments, surface patterning or wrinkling on the surface of the epithelium may be induced upon introduction of fluids, application of negative pressure, or induction by electrical, light, or other stimulatory device. In other embodiments, backing layers or other layers may be added to the neo-epithelium dressing. While the systems 100, 200 and patterned neo-epithelium dressings 106, 206, 306 are shown in the context of epithelium on a wound bed, similar approaches may be taken to pattern the surface of other epithelial or endothelial linings including those within the vascular, respiratory, visual, and digestive systems.

In another embodiment, an interface member may be formed with a thin member coupled to a foam and wherein the thin member contracts after coupling to the foam. The contraction creates the ridges and grooves.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment, and descriptions related one embodiment may be applied to other embodiment as indicated by the context.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A patterned neo-epithelium dressing for treating a skin tissue site having granulation tissue, the patterned neo-epithelium dressing comprising:
   an interface member having a first side; and
   a second, patient-facing side configured to be placed proximate to the granulation tissue,
   the second, patient-facing side of the interface member having a surface topography defined by a plurality of ridges and grooves formed in a pattern to mimic intact human skin.

2. The patterned neo-epithelium dressing of claim 1, wherein the interface member is formed with a fluid passageway that fluidly couples the first side and the second, patient-facing side.

3. The patterned neo-epithelium dressing of claim 1, wherein the interface member has a plurality of pores having an average pore size greater than 5 μm and smaller than 1000 μm.

4. The patterned neo-epithelium dressing of claim 1, wherein the pattern is configured to mimic an intact analogous human skin pattern based on the patient's skin near the wound or a duplicate body part.

5. The patterned neo-epithelium dressing of claim 1, wherein the pattern is configured to mimic a location-specific human skin pattern based on the general features of a specific area of a generic body.

6. The patterned neo-epithelium dressing of claim 1, wherein the interface member comprises a thin member bonded to a foam.

7. The patterned neo-epithelium dressing of claim 1, wherein the interface member comprises:
   a thin member having a first side and a second, patient-facing side;
   a hydrophilic material having a first side and a second, patient-facing side; and
   wherein the second, patient-facing side of the hydrophilic material is coupled to the first side of the thin member.

8. The patterned neo-epithelium dressing of claim 1, further comprising a protein coated on the plurality of ridges and grooves.

9. A method of treating a wound at a tissue site of a patient, the method comprising:
   locating granulation tissue at the tissue site;
   deploying a patterned neo-epithelium dressing on the granulation tissue, the dressing comprising: an interface member having (i) a first side, (ii) a second, patient-facing side, and (iii) the second patient-facing side having a surface topography defined by a plurality of ridges and grooves formed in a pattern configured to mimic intact human skin, and wherein the second, patient-facing side is deployed proximate the granulation tissue; and
   applying a contact pressure on the patterned neo-epithelium dressing.

10. The method of claim 9, wherein the locating comprises promoting the formation of granulation tissue using reduced pressure at the tissue site.

11. The method of claim 10, wherein the step of promoting the formation of granulation tissue comprises applying a reduced-pressure manifold proximate to the tissue site, covering the reduced-pressure manifold with a sealing member, and providing reduced pressure to the reduced-pressure manifold.

12. The method of claim 9, wherein applying the contact pressure comprises:
   deploying a sealing member over the patterned neo-epithelium dressing and a portion of the patient's skin, the sealing member having a first side and a second, patient-facing side; and
   providing reduced pressure to the second, patient-facing side of the sealing member.

13. The method of claim 9, wherein applying the contact pressure comprises deploying a pressure wrap over the first side of the patterned neo-epithelium dressing.

14. The method of claim 9, wherein the interface member has a plurality of pores having an average pore size greater than 5 μm and smaller than 1000 μm.

15. A system for treating a skin tissue site having granulation tissue on a patient, the system comprising:
   a patterned neo-epithelium dressing configured to be disposed proximate to granulation tissue on the skin tissue site, wherein the patterned neo-epithelium dressing comprises: an interface member having (i) a first side, (ii) a second, patient-facing side configured to be placed proximate the granulation tissue, the second, patient-facing side having a surface topography defined by a plurality of ridges and grooves formed in a pattern configured to mimic intact human skin, and (ii) one or more fluid passageways that fluidly couple the first side and the second, patient-facing side;
   a sealing member for placing over the patterned neo-epithelium dressing and the patient's epidermis;
   a reduced-pressure interface fluidly coupled to the sealing member; and
   a reduced-pressure source fluidly coupled to the reduced-pressure interface.

16. The system of claim 15, the interface member has a plurality of pores having an average pore size larger than 5 μm and smaller than 1000 μm.

17. The system of claim 15, wherein the pattern is configured to mimic intact analogous human skin pattern based on the patient's skin near the wound or a duplicate body part.

18. The system of claim 15, wherein the pattern is configured to mimic a location-specific human skin pattern based on a specific area of a generic human body.

19. The system of claim 15, wherein the interface member comprises a polyurethane film bonded to a foam.

* * * * *